US00PP11219P

United States Patent [19]

Strickland

[11] Patent Number: Plant 11,219

[45] Date of Patent: Feb. 15, 2000

[54] LIVE OAK TREE NAMED 'QVTIA'

[75] Inventor: Thomas Julian Strickland, Statesboro, Ga.

[73] Assignee: Tree Introductions, Inc., Bishop, Ga.

[21] Appl. No.: 08/957,959

[22] Filed: Oct. 27, 1997

[51] Int. Cl.[7] ..... A01H 5/00

[52] U.S. Cl. ..... Plt./225

[58] Field of Search ..... Plt./53.7, 225, Plt./216

[56] References Cited

PUBLICATIONS

The New Royal Horticultural Society Dictionary of Gardening, Editor–in–Chief—Anthony Huxley, vol. 3 L to Q, The Stockton Press, New York, p. 788 especially, pp. 776–789, 1992.

*Primary Examiner*—Howard J. Locker

*Assistant Examiner*—Anne Marie Grünberg

*Attorney, Agent, or Firm*—Klarquist Sparkman Campbell Leigh & Whinston, LLP

[57] ABSTRACT

A live oak tree named 'QVTIA' having an upright compact growth habit with a dense foliage canopy, a dominant leader with secondary branches extending upwardly at steep angles and also capable of being reproduced reliably from vegetative cutting.

6 Drawing Sheets

DESCRIPTION

The present invention relates to a new and distinct variety of *Quercus virginiana*, live oak, which has been given the varietal name 'QVTIA'.

I discovered my new tree as a chance seedling growing in a cultivated area in Orangeburg, S.C. in 1993. Although the precise parentage of my new variety is unknown, I am convinced that it is a chance seedling from a *Quercus virginiana* tree. As I observed the parent tree of my new variety, the uniqueness of this tree became apparent because of its more upright and compact growing form.

I observed this first tree of my new variety for a period of time and believe it is particularly useful in landscape fittings where upright compact tree forms are important, such as along trees, building and in planters.

In contrast, although live oak trees are perhaps the most common shade and street tree throughout zones 8–10 of the southern United States, in its entirety it has been represented by seedling material that is variable in growth characteristics and habit. The massive, spreading mature outline, often two to three times its height in common live oak trees results in significant maintenance and pruning problems, particularly when such trees are planted along streets.

Live oak trees offer magnificent ornamental and cultural characteristics, including evergreen foliage, structural integrity, heat tolerance, salt tolerance, urban soil tolerance and pest resistance for the southern United States. Consequently, a new variety of live oak tree which has a more upright, compact growing form, is particularly useful.

My new variety has been asexually propagated from soft wood cuttings at my direction.

This propagation and observation of the resulting progeny have proven the characteristics of my new variety of live oak tree to be firmly fixed. Furthermore, these observations have confirmed that my new variety represents a new and improved variety of live oak tree as particularly evidenced by the unique combination of a compact upright growth habit, a dense foliage canopy, and which can reliably be asexually propagated using vegetative propagation techniques.

The accompanying photographs depict the color of the tree and foliage of my new variety as nearly true as is reasonably possible to make the same in a color illustration of this character.

My 'QVTIA' variety of live oak tree has not been observed under all growing conditions and thus variations may occur as a result of different growing conditions. The following is a detailed description of my new variety of live oak tree with color terminology in accordance with The Royal Horticultural Society Colour Chart (R.H.S.) published by The Royal Horticultural Society of London. The observations are of trees growing in a nursery in Bulloch County, Ga.

My new variety of live oak tree is characterized by its unique upright habit. In 1993, the initially discovered tree of my new variety was two and one-half inches in diameter (measured six inches above ground level). At that time, this first tree was transplanted to a nursery located in Bulloch County, Ga. In October 1997, this initial tree was seven inches in caliper (measured twelve inches above ground level). In October of 1997, the initially discovered tree was twenty-four feet tall and ten feet wide. Its height to width ratio is thus 2.4 to one. This alone distinguishes my new variety from typical *Quercus virginiana* trees. The national champion live oak tree near Lewisburg, La., is fifty-five feet high and one hundred thirty-two feet wide, a height to width ratio of about 0.42. The height to width ratio of the champion live oak tree is no unusual for the species, and serves to emphasize the significantly unique upright growth habit of my new variety.

My new tree maintains a central leader with strongly extending secondary branches forming a compact pyramidal outline. In contrast, seedling live oaks which I have observed do not have a central leader. The unique growth habit insures its capacity for use in areas where lateral growing space is restricted, particularly along streets, where the typical species has been used almost exclusively.

Figure 1:
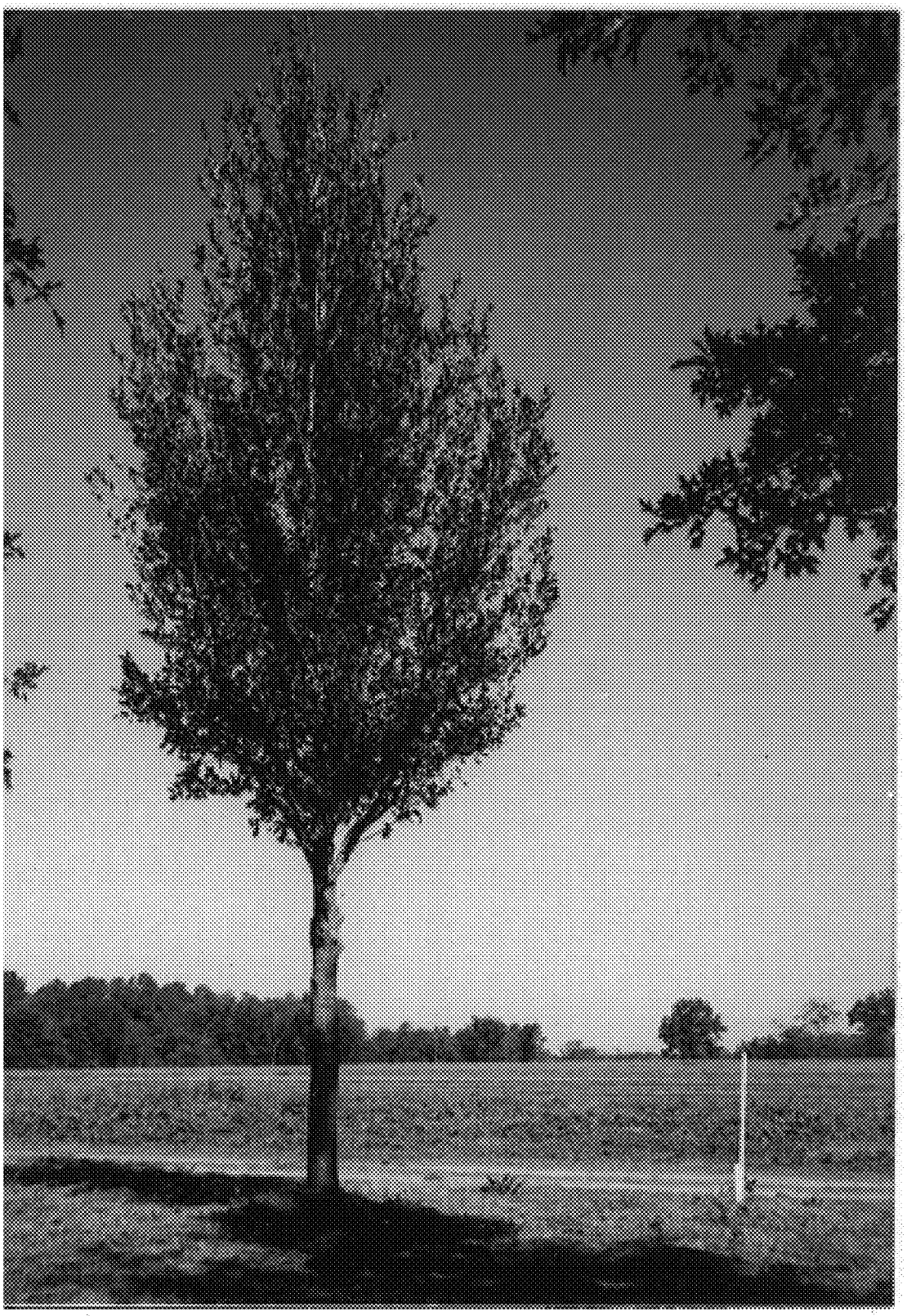
FIG. 1 is a photograph of an entire tree of my new variety.
Figure 2:
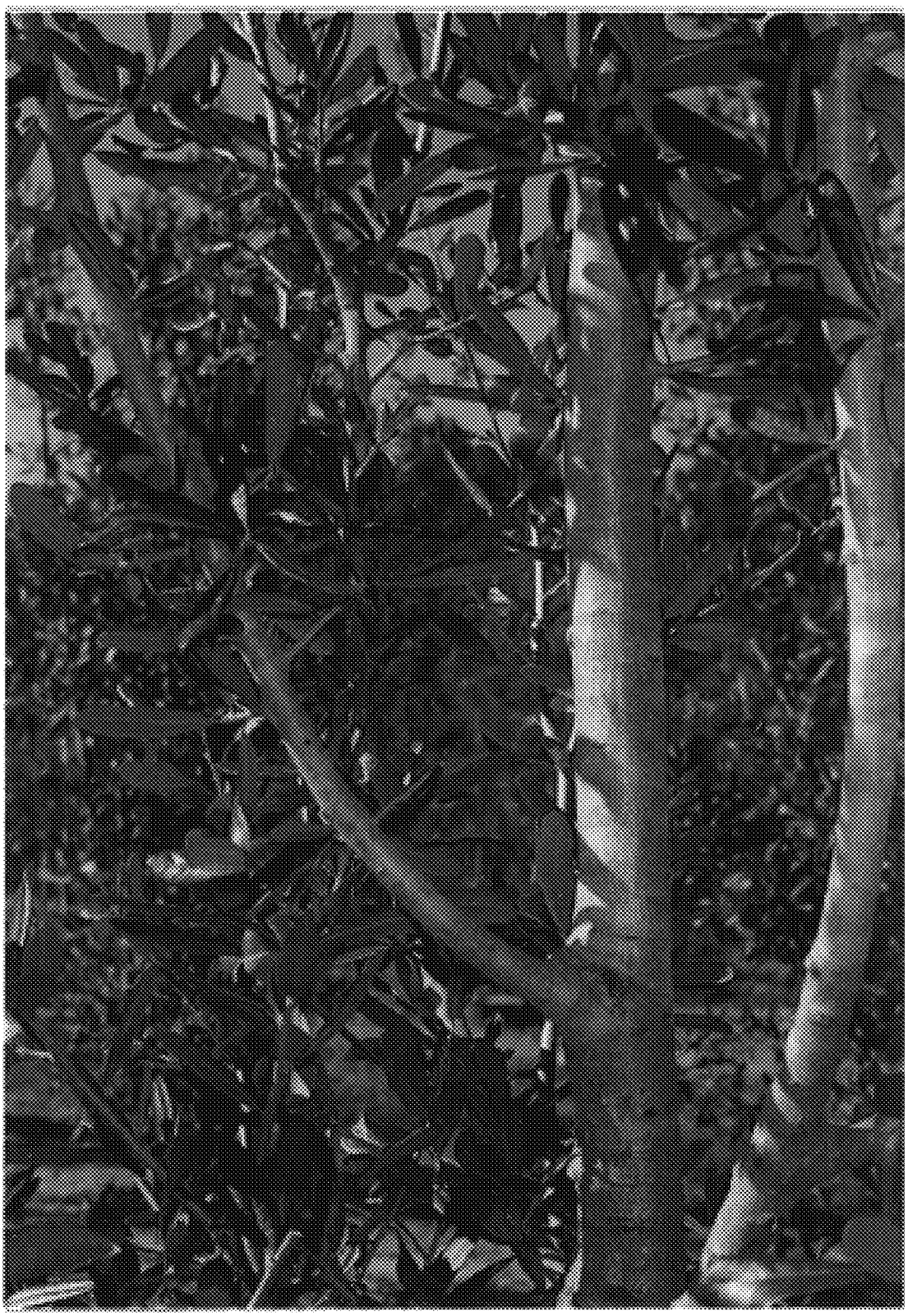
FIG. 2 is a close up of a portion of the main leader and branches of a tree of my new variety showing typical branch angles.
Figure 3:
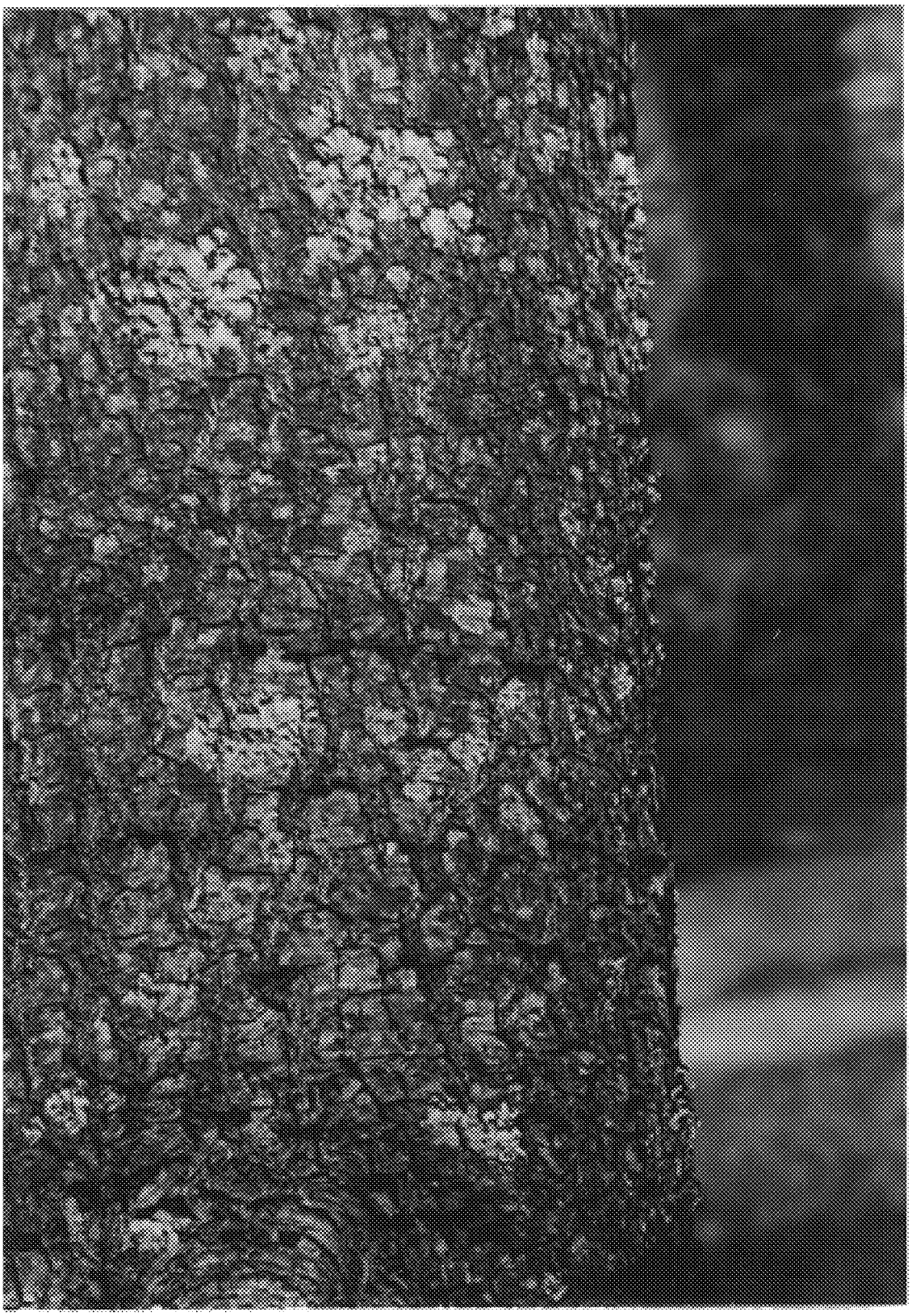
FIG. 3 is a close up of a trunk of my new variety showing mature bark.

More specifically, trees of my new variety have a dominant central leader with secondary branches that emerge at about a fifty to sixty degree angle from vertical and which curve gracefully inwardly. The secondary branches typically end up growing at a thirty to forty degree angle with respect to vertical as they extend upwardly. As a result, as can be seen from FIG. 2, the tree of my new variety has a canopy characterized by close knit branches and full dense foliage. In contrast, traditional seedling live oaks are usually open, splaying and awkward and, in youth, must be pruned often to produce an upright habit. The lower trunk of the initially discovered tree has initiated the scaling and cross checking that is typical of the species as is shown in FIG. 3. Bark colors can vary with greyed-green being typical (Gray-Brown Group R.H.S. 191A). The scaling and cross checking and color observed in the initially discovered tree is common for the species and, although the progeny have not yet exhibited this characteristic, this characteristic is expected to be the same in the asexually reproduced progeny.

Figure 4:
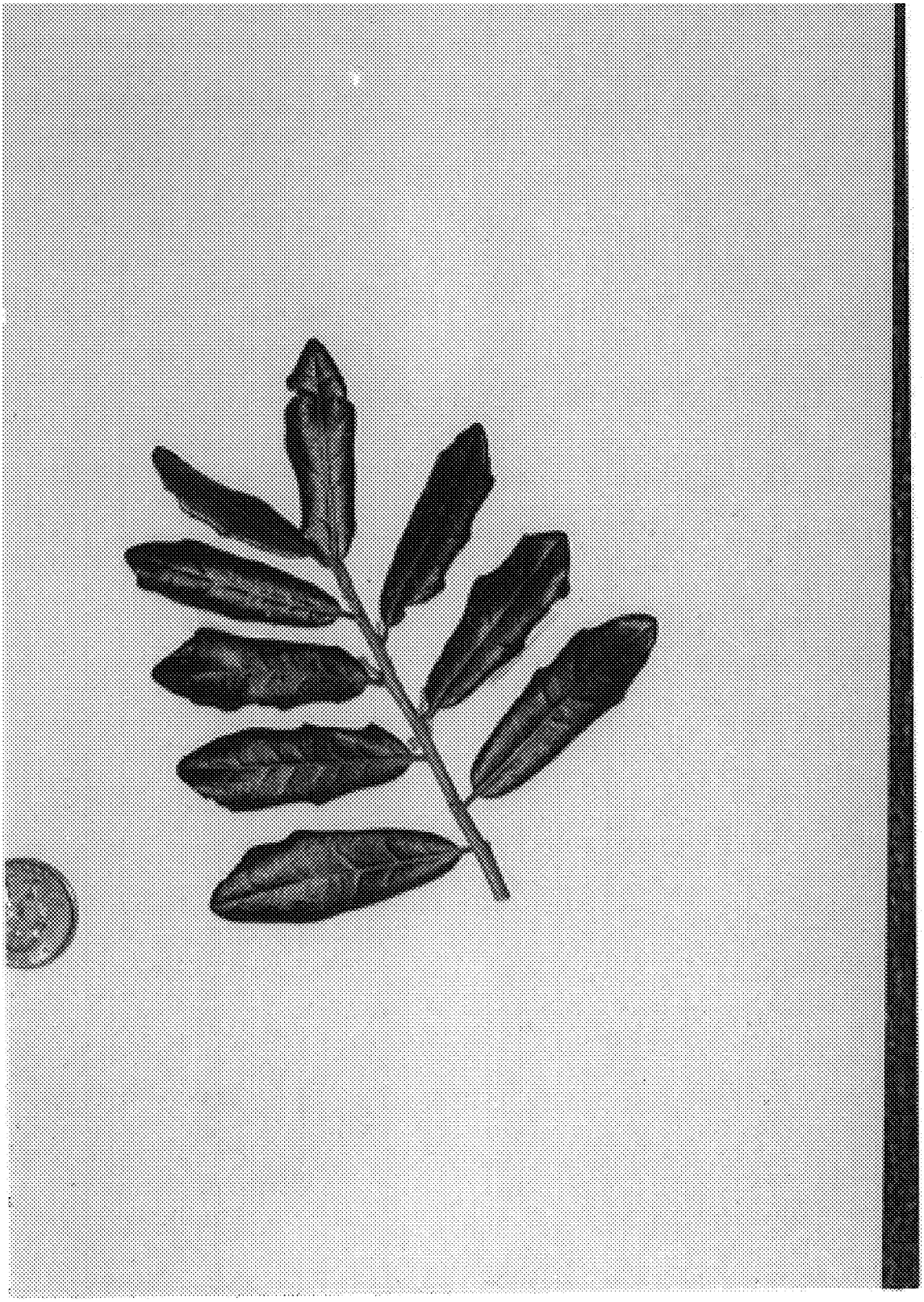
FIG. 4 is a close up of the upper surface of a number of leaves from a tree of my new variety.
Figure 5:
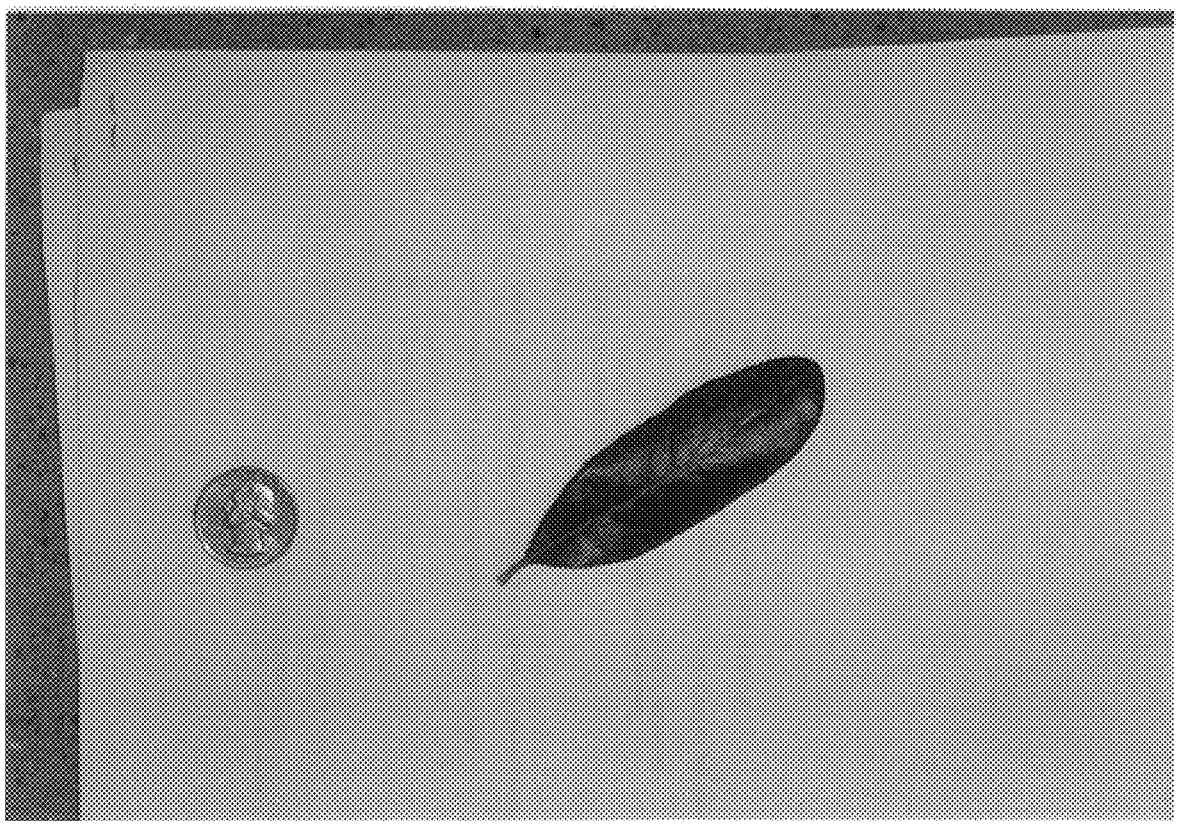
FIG. 5 is a close up of the upper surface of a single leaf from a tree of my new variety.
Figure 6:
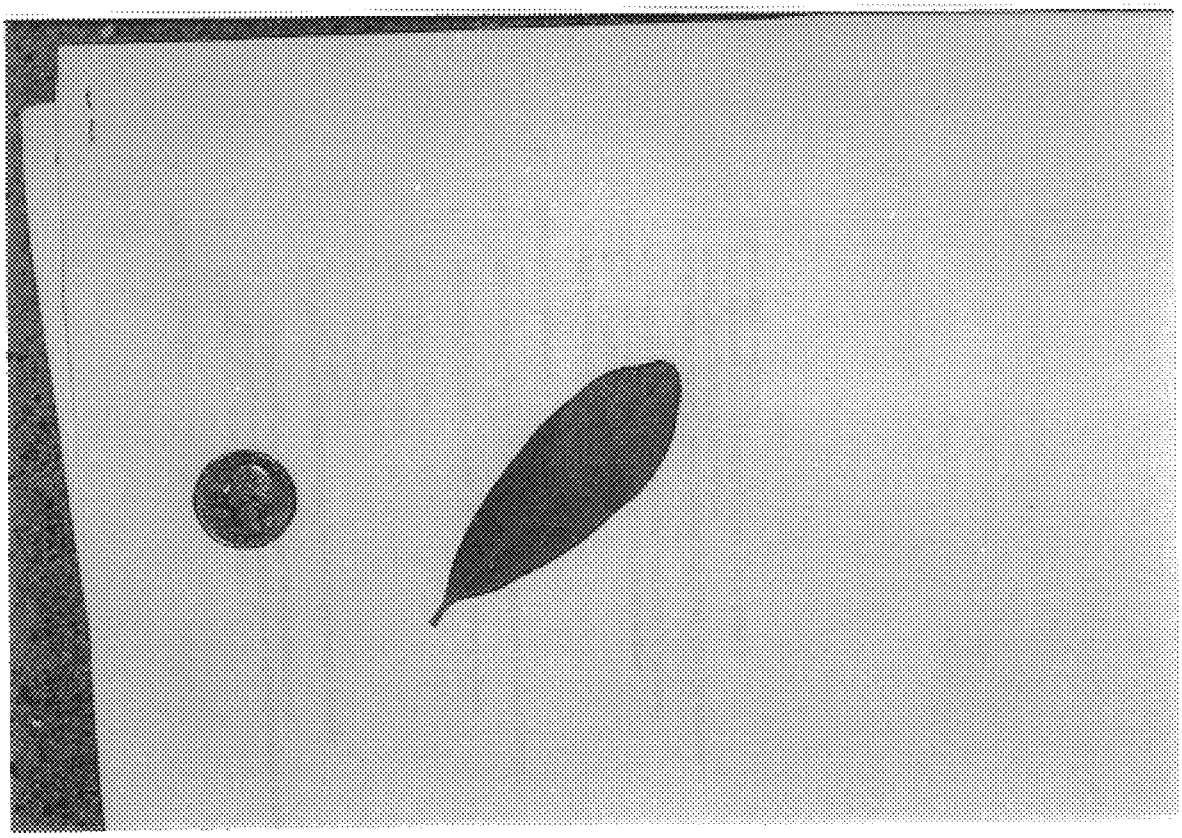
FIG. 6 is a close up of the under surface of a leaf from a tree of my new variety.

The leaves, stems and buds of my new variety insofar as I have been able to observe them, are like those of the species. The leathery leaves are lustrous dark green above, with grayish pubescence on the lower surface. Young branches are pubescent, becoming glabrous with maturity. This characteristic is typical of the species. Buds are imbricate, slightly dome shaped and usually pubescent, having a length between one-sixteenth (1/16) of an inch to less than one-fourth (1/4) of an inch. These are characteristic of the species. Flowers and fruits are typical of the species. My new tree is monoecious, as typical of the genus. Staminate flowers occur in clustered catkins, each flower usually having a two to eight lobed calyx. Pistillate flowers are borne in the axils of the leaves usually in groups of one to five. Each is surrounded by an involuore of scales that eventually become the cap of the acorn. Between one and three fruits will form on a stalk that is usually one-half (1/2) inch in length. The acorn itself is typically three-fourths (3/4) to one (1) inch long and usually about one-half (1/2) as broad with an ellipsoidal cap that covers about one-third (1/3) of the acorn, itself. The ripening acorns are green, becoming dark brown to black and glabrous with age. Fruit sets and ripens in one year, a characteristic typical of live oak. Fruit set first occurred on my new tree in 1993 when the tree was three years old. Leaf shapes are variable, with some showing the holly-like (spiny) margin condition of juvenile live oak trees (FIG. 4). The mature leaves toward the top of the tree are without spines and represent the typical adult leaf of *Quercus virginiana*. Leaves from trees of my new variety have been observed to average two to four inches long, 0.5 to one inch wide, and have petioles averaging 0.25 inch long. The upper leaf surface is a lustrous dark green (Green Group R.H.S. 131A) and glabrous (FIG. 5). The lower leaf (FIG. 6) is covered with grayish woolly pubescence and is gray-green in color (Grayed-Green Group R.H.S. 189A).

THE PLANT

Parentage: Chance live oak seedling of unknown origin, growing in a cultivated area of the Shady Grove Nursery in Orangeburg, S.C.

Tree shape: Upright, compact, pyramidal with uprightly ascending branches.

Trunk: Sturdy, dominant leader.

Bark: Smooth on young stems. The parent tree has been observed to have scaling and cross checking typical of the species.

*Mature bark color.*—(Observed in the parent tree) greyed-green Group R.H.S. 191A.

Branches: Sturdy, very upright in orientation, emerge from a dominant leader at an angle which is typically fifty to sixty degrees relative to vertical, with the branches curving gracefully inwardly as they grow upwardly.

Leaves: Leaf shapes are variable with some having a spiny margin condition and with mature leaves found toward the top of the tree having a smooth margin.The shape of leaves is typical of *Quercus virginiana.*

Leaf surface: Upper leaf surface smooth, lustrous dark green (Green Group R.H.S. 131A) and glabrous. The lower leaf is covered with grayish woolly pubescence and is a gray-green color (Gray-Green Group R.H.S. 189A).

Leaf size: Leaves average two to four inches long, 0.5 to one inch wide, with petiole leaves averaging 0.25 inch long.

Buds, flowers and fruit: Observed to be like those of the species.

I claim:

1. A new and distinct variety of live oak tree substantially as herein shown and described, characterized particularly as to novelty by its upright compact growth habit and dense foliage canopy.

* * * * *